US007078543B2

(12) United States Patent
Cernerud et al.

(10) Patent No.: US 7,078,543 B2
(45) Date of Patent: Jul. 18, 2006

(54) METHODS FOR PRODUCING OXIRANE CARBOXYLIC ACIDS AND DERIVATIVES THEREOF

(75) Inventors: Magnus Cernerud, Stockholm (SE); Kristina Berntsson, Kumla (SE)

(73) Assignee: MediGene Aktiengesellschaft, Planegg/Martinsried (DE)

( * ) Notice: Subject to any disclaimer, the term of this patent is extended or adjusted under 35 U.S.C. 154(b) by 5 days.

(21) Appl. No.: 10/473,503

(22) PCT Filed: Mar. 28, 2002

(86) PCT No.: PCT/EP02/03581

§ 371 (c)(1),
(2), (4) Date: May 24, 2004

(87) PCT Pub. No.: WO02/079178

PCT Pub. Date: Oct. 10, 2002

(65) Prior Publication Data

US 2004/0236103 A1    Nov. 25, 2004

(30) Foreign Application Priority Data

Mar. 30, 2001    (DE) ............................... 101 15 938

(51) Int. Cl.
*C07D 301/24*    (2006.01)
*C07D 301/02*    (2006.01)
(52) U.S. Cl. ...................................... 549/518; 549/549
(58) Field of Classification Search ................ 549/518, 549/549
See application file for complete search history.

(56) References Cited

U.S. PATENT DOCUMENTS

| 4,046,889 | A | 9/1977 | Ondetti et al. |
| 4,172,934 | A | 10/1979 | Heilmann |
| 4,350,633 | A | 9/1982 | Kim et al. |
| 4,450,275 | A | 5/1984 | Arimura et al. |
| 4,692,459 | A | 9/1987 | Ryan et al. |
| 5,739,159 | A | 4/1998 | Wolf |

FOREIGN PATENT DOCUMENTS

| EP | 0 046 590 B1 | 8/1981 |
| EP | 0 198 348 B1 | 10/1986 |
| EP | 0 386 654 A1 | 3/1990 |
| JP | 57046961 A | 3/1982 |
| JP | 01207308 A | 8/1989 |
| WO | WO 82/00643 | 3/1982 |
| WO | WO 82/00645 | 3/1982 |
| WO | WO 90/10002 | 9/1990 |

OTHER PUBLICATIONS

Crilly et al, "Syntheses of Enantiomers of 2-[6-(4-Chlorophenoxy)Hexyl]-Oxirane-2-Carboxylic Acid," *Tetrahedron Letters* 30(7):885-888 (1989).
Crout et al., "Stereoelectronic Control of the Tertiary Ketol Rearrangement: Implications for the Mechanism of the Reaction Catalysed by the Enzymes of Branched-Chain Amino Acid Metabolism, Reductoisomerase and Acetolactate Decarboxylase," *J. Chem. Soc. Perkin Trans 2*, 53-62 (1991).
Jew et al., "Asymmetric Synthesis of (R)-(+)-Etomoxir," *Elsevier Science Ltd.* 8(8):1187-1192 (1997).
Kirkovsky et al., "Chiral Nonsteroidal Affinity Ligands for the Androgen Receptor. 1. Bicalutamide Analogues Bearing Electrophilic Groups in the B Aromatic Ring," *J. Med. Chem* 43:581-590 (2000).
Marhefka et al., "Homology Modeling Using Multiple Molecular Dynamics Simulations and Docking Studies of the Human Androgen Receptor Ligand Binding Domain Bound to Testosterone and Nonsteroidal Ligands," *J. Med. Chem.* 44:1729-1740 (2001).
Prasad et al., "Asymmetrization of 2-Substituted Glycerols: Syntheses of R-Etomoxir and R-Palmoxirate," *Tetrahedron: Asymmetry* 1(7):421-424 (1990).
Sunjic et al., "Asymmetric Hydrogenation of Alpha-Arylpropenoic Acids Catalyzed by Rhodium (I) Complexes of Chiral Ligands Derived from some Monosaccharides," 119(4): 229-233 (1989).
Suzuki et al., "Effects of N-Methacryloyl Amino Acid Applications on Hybrid Layer Formation at the Interface of Intertubular Dentin," *Journal of Dental Research* 77(11):1881-1888 (1998).
Wang et al., "Synthesis and FKBP Binding of Small Molecule Mimics of the Tricarbonyl Region of FK506," *Bioorg. Med. Chem. Lett.* 4(9):1161-1166 (1994).

*Primary Examiner*—Bernard Dentz
(74) *Attorney, Agent, or Firm*—Clark & Elbing LLP

(57)    ABSTRACT

The invention relates to processes for preparing oxiranecarboxylic acids and derivatives thereof, in particular to processes which proceed under stereochemical control of the reaction steps, to the oxiranecarboxylic acids prepared according to the invention and derivatives thereof and to their use in pharmaceutical compositions, in particular for treating hyperlipaemia.

13 Claims, No Drawings

METHODS FOR PRODUCING OXIRANE CARBOXYLIC ACIDS AND DERIVATIVES THEREOF

This application is a national stage entry of PCT/EP02/03581 filed Mar. 28, 2002.

The invention relates to processes/methods for preparing/producing oxiranecarboxylic acids and derivatives thereof, to the oxiranecarboxylic acids prepared according to the invention and to their use in pharmaceutical compositions.

Hitherto, oxiranecarboxylic acids and derivatives thereof have been used, for example, for treating cardiac insufficiency and coronary heart disease, as described, for example, in WO 95/15161, or else for treating diabetes (WO 82/00645). (+)-Etomoxir, in particular, is suitable for treating hyperlipaemia.

The processes described in the literature for preparing oxiranecarboxylic acids and derivatives thereof can only be carried out on a laboratory scale, so that the oxiranecarboxylic acids and derivatives thereof can not be provided in sufficient amounts at low cost.

EP-A 0 386 654 describes a process for preparing racemic oxiranecarboxylic acids which have to be separated after the synthesis to yield the pure enantiomers.

A key step in the synthesis of oxiranecarboxylic acids is the construction of the stereocentre and the cyclization to give the oxirane. In the literature, various processes have been described for this purpose. Thus, for example, the publication "Asymmetrization of 2-substituted glycerols: Syntheses of R-Etomoxir and R-Palmoxirate" by K. Prasad et al., Tetrahedron: Asymmetry, 1990, 1, 421–424, describes a synthesis starting from 2-substituted glycerol involving an enantioselective hydrolysis with the use of hydrolytic enzymes. The yield of the key step is about 45%.

EP-B 0 046 590 describes a process for preparing phen(alk)oxy-substituted oxiranes in which the oxirane is introduced into the molecule by oxidation of a C—C double bond. The crude product then requires a complicated chromatographic purification.

M. M. H. Crilley et al. (Tetrahedron Lett., 1989, 30, 885) describe a synthesis involving a sharpless epoxidation, with a yield of 49% in this key step.

The article "Asymmetric synthesis of (R)-(+)-etomoxir" by S. Jew et al., Tetrahedron: Asymmetry, 1997, 8, 1187–1192, describes a 10-step synthesis which yields etomoxir in amounts of 30 mg. The synthesis employs diazomethane, which renders this process unsuitable for a large-scale synthesis. In addition, in this synthesis, the substituent on the side-chain is modified after the cyclization to the oxirane, i.e. after the construction of the stereocentre. This means that even during the further course of the reaction, the stereochemistry has to be strictly controlled to avoid complicated purification steps and separation problems.

None of the processes hitherto utilized for preparing oxiranecarboxylic acids and derivatives thereof is suitable for a large-scale synthesis, in particular since expensive and dangerous starting materials or auxiliaries are employed and since the stereochemistry has to be controlled over a large number of synthesis steps.

Accordingly, it was the primary object of the present invention to provide a process for preparing oxiranecarboxylic acids and derivatives thereof where a synthesis is carried out on an industrial scale using inexpensive raw materials obtainable in a simple manner and in large amounts.

According to the invention, this object is achieved by a process for preparing oxiranecarboxylic acids and derivatives thereof, comprising the synthesis of a compound of the formula (VIII)

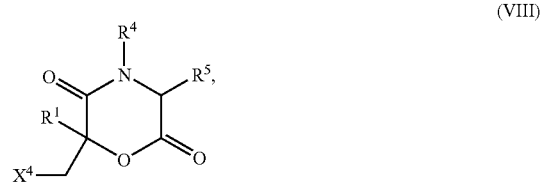

(VIII)

in which
  $R^1$ is a straight-chain or branched mono-, poly- or unsubstituted alkyl group, a straight-chain or branched mono-, poly- or unsubstituted alkylene group, a straight-chain or branched mono-, poly- or unsubstituted aralkyl, alkylaryl or aryl group,
  the radicals $R^4$ and $R^5$ are identical or different straight-chain or branched mono-, poly- or unsubstituted alkyl groups, straight-chain or branched mono-, poly- or unsubstituted alkylene groups, straight-chain or branched mono-, poly- or unsubstituted aralkyl, alkylaryl or aryl groups, where $R^4NCR^5$ may be part of a substituted or unsubstituted cyclic structure which may also contain a further heteroatom selected from the group consisting of N, S and O,
  $X^4$ is a functional group capable of forming a cationic intermediate in a reaction with a C—C double bond and is a good leaving group, and
  $R^1$ and $R^4NCR^5$ are not simultaneously —$(CH_2)_6$—OBn and an unsubstituted five-membered ring, respectively, comprising the steps
  (a) of reacting a compound of the formula (V) with an amine of the formula (VI) to give a compound of the formula (VII)

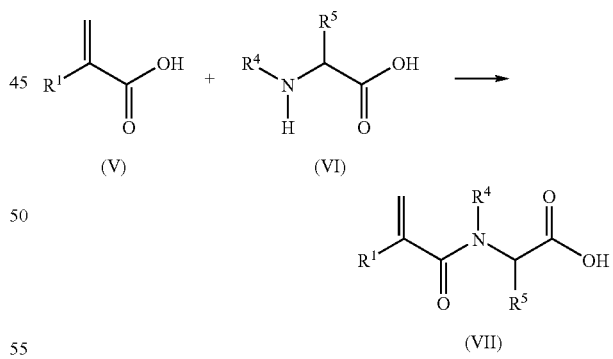

in which the radicals $R^1$, $R^4$ and $R^5$ are as defined above; and
  (b) converting a compound of the formula (VII) into a lactone of the formula (VIII).

A particular advantage of the process according to the invention is the fact that oxiranecarboxylic acids and derivatives thereof can be prepared on an industrial scale, i.e. on a kilogram scale.

In the context of the present invention, oxiranecarboxylic acids and derivatives thereof are understood as meaning oxiranecarboxylic acids of the formula (X) and their esters with C1- to C15-alcohols and the pharmacologically acceptable salts of the carboxylic acids. Suitable salts are salts with inorganic and organic bases. Cations suitable for use in the salt formation are especially the cations of the alkali metals, alkaline earth metals or earth metals. Salts of lithium, sodium, potassium, magnesium, calcium and aluminium may be mentioned by way of example. However, it is also possible to use the corresponding cations of organic nitrogen bases, such as amines, amino alcohols, amino sugars, basic amino acids, etc. Salts of ethylenediamine, dimethylamine, diethylamine, morpholine, piperidine, piperazine, N-methylpiperazine, methylcyclohexylamine, benzylamine, ethanolamine, diethanolamine, triethanolamine, tris(hydroxymethyl)-aminoethane, 2-amino-2-methylpropanol, 2-amino-2-methyl-1,3-propanediol, glucamine, N-methylglucamine, glucosamine, N-methylglucosamine, lysine, ornithine, arginine and quinoline may be mentioned by way of example.

For the reaction according to step (a), the carboxylic acid of the formula (V) is preferably initially activated. An activation can be carried out, for example, by forming a carboxylic anhydride, an activated carboxylic ester or a carbonyl halide. For the industrial synthesis in the context of the present invention, activation as carbonyl chloride is particularly preferred.

The compound of the formula (V) is reacted with a suitable reagent capable of forming carbonyl chlorides, such as, for example, an organic or inorganic acid chloride. Use is made, in particular, of oxalyl chloride, $PCl_5$, $PCl_3$ and thionyl chloride. The reaction can be carried out with or without organic solvent, preferably with addition of dimethylformamide (DMF) at temperatures of from 0 to 60° C., preferably from 15 to 50° C., particularly preferably from 20 to 30° C. Typical reaction times are 0.5 to 3, in particular 1 to 2, hours.

The reaction of the preferably activated carboxylic acid with the amine of the formula (VI) is carried out at basic pH in polar solvents, such as water, alcohols, ketones or ethers, or else in mixtures of different solvents, in particular in mixtures of water and acetone, water and methanol or water and ethanol. To adjust the desired pH, use is made, in particular, of inorganic bases, such as alkali metal hydroxides or alkoxides, in particular potassium hydroxide or sodium hydroxide. The reaction is carried out at temperatures of from –10 to 40° C., preferably from 0 to 20° C. A typical reaction time is up to 1.5 hours, in particular from 0.5 to 1 hour.

For the reaction according to step (b), a reagent is used which can release a species which is capable of forming a cationic intermediate having a double bond, in particular a C—C double bond, and simultaneously forms a good leaving group. The cationic intermediate formed having the double bond can then be attacked by a nucleophile, preferably intramolecularly, so that a lactone of the formula (VIII) is formed.

Reagents suitable for such a reaction are in particular those releasing halogen cations, preferably N-bromosuccinimide, N-iodosuccinimide or N-chlorosuccinimide. The reaction is preferably carried out in polar organic solvents, in particular alcohols, such as ethanol, methanol or propanol, or else in solvent mixtures with addition of DMF. Here, the pH is above 7. This is preferably achieved by adding inorganic alkali metal salts, in particular hydroxides or alkoxides, such as sodium hydroxide, potassium hydroxide or potassium tert-butoxide. The reaction is typically carried out at temperatures of from –10 to 10° C., in particular at below 5° C., for 10 to 24, preferably 12 to 17, hours. The product of the reaction is preferably purified by crystallization.

In the context of the invention, it is also envisaged that the reaction according to step (b) is carried out with control of the stereochemistry.

In the context of the present invention, the radical $R^1$ can have a structure of the formula (1)

$$—(CR'R'')_n—Z_m—Ar \qquad (1),$$

in which

Ar represents a substituted or unsubstituted phenyl radical, a substituted or unsubstituted 1- or 2-naphthyl radical or a substituted or unsubstituted heterocyclic ring, which preferably has 5 members and is selected from the group consisting of thiophene, thiazole, isothiazole, pyrrole and particularly preferably pyrazole, R' and R'' represent hydrogen or fluorine or a methyl radical, Z represents —$P(CR'R'')_o$— where P is oxygen or sulphur and o is an integer from 0 to 4, in particular 1 or 2, m is an integer from 0 to 2, preferably 0 or 1, and n is an integer from 2 to 8, in particular an integer from 4 to 6.

The radical $R^1$ is preferably a radical having 1 to 20 carbon atoms, in particular with halogen substituents, preferably fluorine. Furthermore, $R^1$ preferably has a structure of the formula (1a)

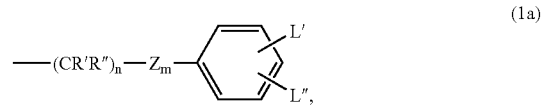

in which

R' and R'' are hydrogen or fluorine or a methyl radical,

L' and L'' independently of one another are hydrogen, halogen, a substituted or unsubstituted branched or straight-chain alkyl, aryl or alkylaryl group, a substituted or unsubstituted branched or straight-chain alkoxy or aryloxy group, a substituted or unsubstituted branched or straight-chain carboxyalkyl or carboxyaryl group, a nitro group or a trifluoromethyl group, and Z is —$P(CR'R'')_o$— where P is oxygen or sulphur and o is an integer from 0 to 4, in particular 1 or 2, m is an integer from 0 to 2, preferably 0 or 1, and n is an integer from 2 to 8, in particular an integer from 4 to 6.

In particular, L' or L'' is hydrogen and the respective other substituent L' or L'' represents a halogen atom, preferably chlorine or fluorine, in particular chlorine. In a particularly preferred embodiment, m and o are 1, n is 6 and P is oxygen.

The radical $X^4$ is preferably a halogen atom selected from the group consisting of chlorine, bromine and iodine, particular preference is given to bromine.

The radicals $R^4$ and $R^5$ represent in particular alkyl radicals having 1 to 10 carbon atoms, preferably having 1 to 6 carbon atoms, which are preferably unsubstituted or fluorine-substituted. In the context of the present invention, $R^4$ and $R^5$ can also preferably be part of a substituted or unsubstituted cyclic structure $R^4NCR^5$ which may also contain a further heteroatom selected from the group consisting of N, S and O, in particular a five- or six-membered ring.

The amine of the formula (VI) is in particular a cyclic amine having 5 or 6 ring atoms, in particular proline or a derivative thereof. In a particularly preferred embodiment of the invention, the amine of the formula (VI) has a stereocentre; particularly preferably, the amine of the formula (VI) is L-proline.

In a particularly preferred embodiment, the invention relates to a process where the compound of the formula (V) is obtained by reacting a compound of the formula (IV)

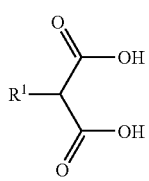

(IV)

where in the formula (IV) $R^1$ is a straight-chain or branched mono-, poly- or unsubstituted alkyl group, a straight-chain or branched mono-, poly- or unsubstituted alkylene group, a straight-chain or branched mono-, poly- or unsubstituted aralkyl, alkylaryl or aryl group.

This is a reaction of the carboxylic acid with a reagent which results in a reduction with formation of a C—C double bond. Suitable here are those reagents which attack only one of the acid functions. The reaction can be carried out, for example, using formaldehyde, in particular paraformaldehyde, and an organic base, such as, for example, triethylamine, diisopropylethylamine or piperidine, in particular piperidine, in organic solvents, such as alcohols, in particular methanol, ethanol, propanol or mixtures thereof, in particular in isopropanol. The reaction is carried out at temperatures of from 40 to 60° C., in particular from 45 to 55° C., until the proportion of unreacted starting material according to HPLC is below 2%, preferably below 1%, particularly preferably below 0.5%.

In a further embodiment, the invention relates to a process where the compound of the formula (IV) is obtained by hydrolysing the compound of the formula (III)

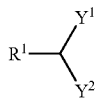

(III)

in which $R^1$ is a straight-chain or branched mono-, poly- or unsubstituted alkyl group, a straight-chain or branched mono-, poly- or unsubstituted alkylene group, a straight-chain or branched mono-, poly- or unsubstituted aralkyl, alkylaryl or aryl group, and $Y^1$ and $Y^2$ are identical or different electron-withdrawing groups which can be converted into a carboxylic acid.

According to the invention, the radicals $Y^1$ and $Y^2$ are preferably selected from the group consisting of CN, carboxylic acid, carboxylic anhydride and carboxylic ester with a C1- to C10-alcohol. In the context of the present invention, the radicals $Y^1$ and $Y^2$ are in particular radicals of the general structure —$CO_2R^2$ and —$CO_2R^3$, where $R^2$ and $R^3$ represent a mono-, poly- or unsubstituted alkyl radical having 1 to 20, preferably 1 to 10, particularly preferably 1 to 4, carbon atoms, in particular unsubstituted or fluorine-substituted.

Suitable for this hydrolysis are all methods known to the person skilled in the art, in particular acidic or basic hydrolysis. In the context of the present invention, basic hydrolysis employing alkali metal hydroxide or alkoxide, in particular sodium hydroxide or potassium hydroxide, in organic polar solvents, such as alcohols, ketones or ethers, in particular cyclic ethers, or in water or in mixtures of two or more thereof, such as, for example, methanol/water, tetrahydrofuran/water or ethanol/water, if appropriate with the use of phase-transfer catalysts, is preferred. The reaction is preferably carried out at temperatures of from 10 to 60° C., in particular from 40 to 50° C., particularly preferably at from 20 to 30° C., for 1 to 24, in particular 1 to 3, hours.

A further embodiment of the invention comprises a process where the compound of the formula (III) is obtained by condensing a compound of the formula (I) with a compound of the formula (II)

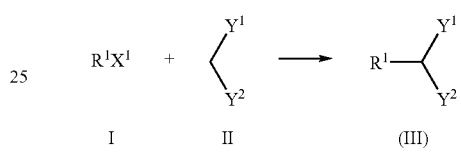

I  II  (III)

where $R^1$ is a straight-chain or branched mono-, poly- or unsubstituted alkyl group, a straight-chain or branched mono-, poly- or unsubstituted alkylene group, a straight-chain or branched mono-, poly- or unsubstituted aralkyl, alkylaryl or aryl group, $X^1$ is a leaving group, $Y^1$ and $Y^2$ are identical or different electron-withdrawing groups which can be converted into a carboxylic acid.

In the context of the invention, the substituent $X^1$ is preferably a halogen atom, a tosylate group or a triflate group, in particular chlorine or bromine.

The condensation reaction is carried out in the presence of a compound capable of deprotonating a compound of the formula (II). According to the invention, use is made, in particular, of inorganic bases, such as alkali metal alkoxides or carbonates, preferably potassium carbonate or sodium ethoxide. The reaction is carried out in polar solvents, such as, for example, alcohols, ketones or ethers, preferably with addition of DMF, at temperatures of from 90 to 150° C., in particular from 110 to 130° C., for 10 to 20, preferably 12 to 18, hours.

In addition, a preferred embodiment of the invention relates to a process where the compound $R^1$-$X^1$ is obtained by reacting a straight-chain or branched mono- or polysubstituted alkane having two leaving groups $X^1$ and $X^2$ with a mono-, poly- or unsubstituted benzene derivative, preferably a phenol derivative.

This reaction is carried out under conditions permitting a reaction of the benzene derivative, in particular the phenol, in the sense of a substitution reaction, preferably under basic conditions. The basic conditions can be set, for example, by adding a hydroxide, an alkoxide or a carbonate, in particular by adding sodium carbonate or potassium carbonate. The alkane used is preferably simultaneously used as solvent, if appropriate with addition of DMF. In the context of the invention, the reaction is carried out at temperatures of from 100 to 130° C., in particular at from 115 to 125° C., for 2 to 8, preferably 3 to 6, hours.

In the context of the invention, preference is given to alkanes having a general structure $X^1$—$(CR'R'')_n$—$Z_m$—$X^2$ where R' and R'' represent hydrogen or fluorine, Z represents —$P(CR'R'')_o$— where P is oxygen or sulphur and o is an integer from 0 to 4, in particular 1 or 2, $X^1$ and $X^2$ are good leaving groups, preferably independently of one another selected from the group consisting of halogen, triflate and tosylate, in particular chlorine or bromine, m is an integer from 0 to 1, preferably 0, and n is an integer from 2 to 8, in particular an integer from 4 to 6.

In the context of the invention, it is possible, in particular, that $X^1$ and $X^2$ are identical. In this case, in the substitution reaction no product mixtures difficult to separate are formed. In the context of the invention, the alkane is in particular employed in excess. The unreacted alkane can be recovered.

In one possible embodiment of the present invention, the starting material used can be epsilon-caprolactone, a cheap starting material with low toxicity. Epsilon-caprolactone can be converted into various 1,6-bifunctional structures with 6 carbon atoms. Such bifunctional structures have two different substituents, allowing selective transformation of one of the two ends.

There are a number of options for opening the ring of the epsilon-caprolactone. The ring opening can be carried out by amidation using, for example, benzylamine (solvent, for example: toluene, tetrahydrofuran or xylene), ethanolamine (preferably without additional solvent, since ethanolamine for its part acts as a solvent), dibutylamine or isopropylbenzylamine, or else by esterification or nucleophilic ring opening, preferably using hydrogen bromide, which results in the formation of 6-bromohexanoic acid.

Advantageously, 6-bromohexanoic acid is formed by distilling epsilon-caprolactone in, for example, 48% strength hydrobromic acid, for about 3–4 hours. The reaction mixture is then diluted and mixed, for example, with toluene, and the acidic phase is then separated off. Last acid residues can be removed, for example, by azeotropic distillation. After the end of distillation, a two-fold excess of alcohol, for example methanol, ethanol or n-propanol, is added, and the excess alcohol is removed again by distillation.

In the context of the present invention, it is possible to use both the bromoesters obtained in this manner, and the free acids.

The benzene derivative is preferably a phenol derivative, in particular a phenol having one or two further substituents on the aromatic ring. Preferred substituents are, for example, halogen, an alkyl or alkoxy group, a nitro group or a trifluoromethyl group, in particular chlorine.

In the context of the invention, it is also possible to use the compound of the formula (VIII) in a reaction where a compound of the formula (IX) is formed

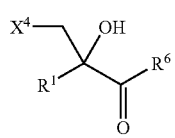

(IX)

in which $R^1$ is a straight-chain or branched mono-, poly- or unsubstituted alkyl group, a straight-chain or branched mono-, poly- or unsubstituted alkylene group, a straight-chain or branched mono-, poly- or unsubstituted aralkyl, alkylaryl or aryl group, $X^4$ is a functional group capable of forming a cationic intermediate in a reaction with a C—C double bond and is a good leaving group, and $R^6$ is selected from the group consisting of OH, $O^-M^+$, $O^-M^{2+}$, where M is an alkali metal, an alkaline earth metal or an earth metal or a cation of an organic nitrogen base, and OR, where R is a substituted or unsubstituted alkyl or alkylene radical having 1 to 15 carbon atoms.

In the context of the present invention, $R^6$ is preferably selected from the group consisting of OH, $O^-Na^+$, $O^-K^+$, OR, where R is an unsubstituted alkyl radical having 1 to 10 carbon atoms.

The compound of the formula (IX) can be obtained, for example, by hydrolysis. In principle, all methods known to the person skilled in the art are suitable. Particular preference is given to acid hydrolysis with addition of mineral acids, such as, for example, hydrochloric acid or sulphuric acid. According to the invention, the reaction is carried out in polar solvents, such as water or alcohols, in particular water, at temperatures above 80° C., preferably at 100° C., for at least 24 hours, preferably for at least 36 hours, particularly preferably for at least 48 hours.

Moreover, in the context of the present invention, it is possible to use the compound of the formula (IX) in a reaction where an oxirane of the formula (X)

(X)

is obtained in which $R^1$ is a straight-chain or branched mono-, poly- or unsubstituted alkyl group, a straight-chain or branched mono-, poly- or unsubstituted alkylene group, a straight-chain or branched mono-, poly- or unsubstituted aralkyl, alkylaryl or aryl group, and $R^6$ is selected from the group consisting of OH, $O^-M^+$, $O^-M^{2+}$, where M is an alkali metal, an alkaline earth metal or an earth metal or a cation of an organic nitrogen base, and OR, where R is a substituted or unsubstituted alkyl or alkylene radical having 1 to 15 carbon atoms.

The reaction for forming the oxirane takes place under conditions which permit the intramolecular attack of the OH group in the sense of a substitution reaction. According to the invention, the reaction is carried out in a basic medium, a suitable pH being established, for example, by addition of hydroxide or alkoxide, in particular by addition of potassium tert-butoxide. The reaction can take place in polar solvents, such as water, alcohols, ketones, ethers, preferably MTBE, or else in mixtures of two or more of these solvents. Particular preference is also given to carrying out the reaction in a dried and concentrated solution of a nonpolar solvent, such as toluene from the previous reaction step (see Example 5). In the context of the invention, the reaction is carried out at temperatures of from −10 to 10° C., in particular temperatures below 5° C., for 0.5 to 2.5, preferably 1 to 2, hours. Whether the reaction has gone to completion can be checked, for example, by HPLC.

However, in the context of the present invention it is also possible that, after cyclization, for example, a salt of an oxiranecarboxylic acid is present which is then converted in a further reaction step into a carboxylic ester, in particular an ester with an alcohol having 1 to 15 carbon atoms, preferably 1 to 10 carbon atoms, particularly preferably 1 to 6 carbon atoms. Suitable reaction conditions for the esterification are described, for example, in "Organikum", 18$^{th}$ edition, 1990, Deutscher Verlag der Wissenschaften, Berlin, 400–408.

The invention relates in particular to a process which can be described by the following scheme, where the radicals $R^1$, $R^4$, $R^5$, $R^6$, $X^1$, $X^2$, $X^4$, $Y^1$ and $Y^2$ are as defined above. R represents H or a substituted or unsubstituted alkyl or alkylene radical having 1 to 15 carbon atoms. $X^3$ is preferably a radical which corresponds to the definition of L', particularly preferably a halogen, in particular chlorine:

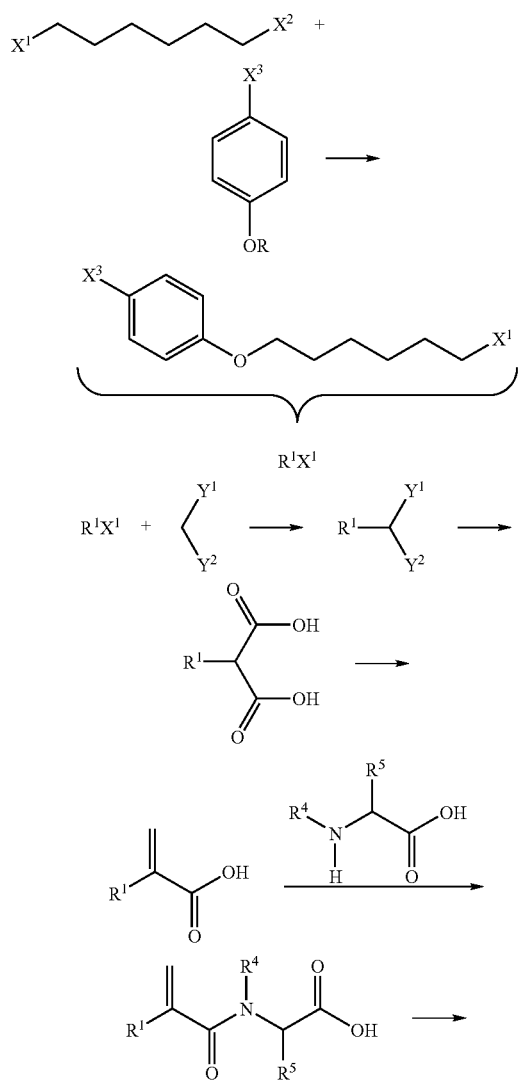

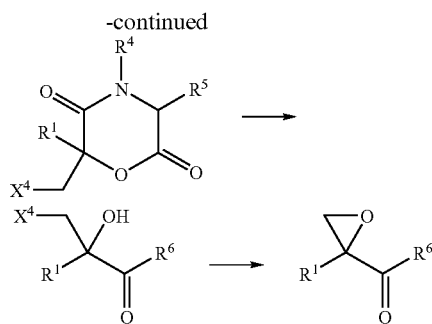

In the embodiment described above, an oxiranecarboxylic acid or a derivative thereof is obtained in eight synthesis steps from readily available starting materials. The last reaction step is the cyclization, so that it is not necessary to carry out further reaction steps with the reactive oxirane.

The invention also provides a process for preparing oxiranecarboxylic acids and derivatives thereof, comprising the synthesis of a compound of the formula (IX), comprising the conversion of a compound of the formula (VIII) into the compound of the formula (IX)

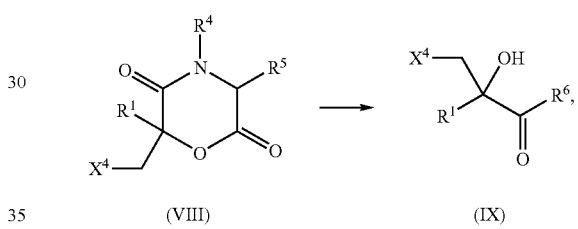

(VIII)                    (IX)

where
  $R^1$ is a straight-chain or branched mono-, poly- or unsubstituted alkyl group, a straight-chain or branched mono-, poly- or unsubstituted alkylene group, a straight-chain or branched mono-, poly- or unsubstituted aralkyl, alkylaryl or aryl group,
  the radicals $R^4$ and $R^5$ are identical or different straight-chain or branched mono-, poly- or unsubstituted alkyl groups, straight-chain or branched mono-, poly- or unsubstituted alkylene groups, straight-chain or branched mono-, poly- or unsubstituted aralkyl, alkylaryl or aryl groups, where $R^4NCR^5$ may be part of a substituted or unsubstituted cyclic structure which may also contain a further heteroatom selected from the group consisting of N, S and O,
  $X^4$ is a functional group capable of forming a cationic intermediate in a reaction with a C—C double bond and is a good leaving group, and
  $R^1$ and $R^4NCR^5$ are not simultaneously —(CH$_2$)$_6$—OBn and an unsubstituted five-membered ring, respectively, and
  $R^6$ is selected from the group consisting of OH, O$^-$M$^+$, O$^-$M$^{2+}$, where M is an alkali metal, an alkaline earth metal or an earth metal or a cation of an organic nitrogen base, and OR, where R is a substituted or unsubstituted alkyl or alkylene radical having 1 to 15 carbon atoms.

Further reaction steps of this process may, in particular, be the steps described in more detail above.

In addition, the invention also relates to a process for preparing oxiranecarboxylic acids and derivatives thereof, comprising the synthesis of a compound of the formula (X), comprising a reaction of a compound of the formula (IX) in which an oxirane of the formula (X) is formed $$X^4\text{—}\underset{R^1}{\underset{|}{C}}(OH)\text{—}\underset{\underset{O}{\|}}{C}\text{—}R^6 \longrightarrow \underset{R^1}{\triangle}\underset{\underset{O}{\|}}{C}\text{—}R^6,$$

(IX)      (X)

where
- $R^1$ is a straight-chain or branched mono-, poly- or unsubstituted alkyl group, a straight-chain or branched mono-, poly- or unsubstituted alkylene group, a straight-chain or branched mono-, poly- or unsubstituted aralkyl, alkylaryl or aryl group,
- $R^1$ is not $-(CH_2)_6-OH$,
- $X^4$ is a functional group capable of forming a cationic intermediate in a reaction with a C—C double bond and is a good leaving group, and
- $R^6$ is selected from the group consisting of OH, $O^-M^+$, $O^-M^{2+}$, where M is an alkali metal, an alkaline earth metal or an earth metal or a cation of an organic nitrogen base, and OR, where R is a substituted or unsubstituted alkyl or alkylene radical having 1 to 15 carbon atoms.

Further embodiments of this process may comprise the reaction steps described in more detail above.

In the context of the present invention, it is also possible that a process according to the invention takes place with stereochemical control of the individual reaction steps.

The compounds prepared according to the invention may contain a centre of chirality. Accordingly, the invention embraces both the racemates and the enantiomers and their mixtures. For racemate separation, methods known to the person skilled in the art are employed. If the process takes place under stereochemical control, it is possible to prepare the (+)-enantiomers of the compounds, for example by using chiral auxiliaries. The chiral auxiliaries used are, in particular, chiral amino acids; for example, the compound (VI) used can be L-proline, in particular. However, in the context of the present invention it is also possible to prepare the (−)-enantiomers.

In a preferred embodiment, the present invention relates to a process for preparing etomoxir, palmoxirate or clomoxir, in particular (+)-etomoxir.

The invention furthermore also provides the compounds prepared by a process according to the invention, in particular the oxiranecarboxylic acids and derivatives thereof, which can be prepared by the processes according to the invention. In addition, the invention also relates to compounds of the formula (VII), preparable by step (a) of a process according to the invention.

The invention furthermore relates to the use of an oxiranecarboxylic acid prepared according to the invention or a derivative thereof in pharmaceutical compositions, in particular to the use of the oxiranecarboxylic acids prepared according to the invention and derivatives thereof for treating disorders associated with glucose metabolism, lipid metabolism, cardiovascular disorders and cardiac insufficiency. Specifically, these are, for example, diabetes, hyperlipaemia, coronary heart disease such as angina pectoris or myocardial infarction, states after myocardial infarction or dilatative cardiomyopathies.

Below, the invention is illustrated in more detail by exemplary syntheses.

DETAILED DESCRIPTION

EXAMPLES

Example 1

1. Formation of $R^1\text{—}X^1$: 6-(4-chlorophenoxy)hexyl chloride (6-CPHC) in 1,6-dichlorohexane Substances used:

| | | | |
|---|---|---|---|
| 4-Chlorophenol | 31.5 kg | 1 eq. | 245 mol |
| 1,6-Dichlorohexane | 280 l | 7.9 eq. | 1.93 kmol |
| Potassium carbonate | 44 kg | 1.3 eq. | 318 mol |
| DMF (dimethylformamide) | 75 kg | | |
| n-Heptane | 200 kg | | |
| Water | 390 l | | |

4-Chlorophenol (as a melt) was added to 1,6-dichlorohexane, followed by DMF. Potassium carbonate was added to the mixture. The resulting viscous mixture was heated at about 120° C. The reaction was continued for 3–6 hours until HPLC showed that the proportion of 4-chlorophenol was below 1 area %.

Once the reaction had been deemed to be complete, the reaction mixture was cooled to about 60° C. The solid was filtered off. The filter cake was washed with DMF (about 20 l).

Potassium carbonate (15 kg), n-heptane (200 kg) and water (235 l) were added to the combined mother liquor and washing solution. The temperature of the resulting two-phase mixture was adjusted to 60° C., and the aqueous phase was removed. The organic phase was washed with water (155 l) at about 60° C.

The organic phase that remained was concentrated under reduced pressure at about 100° C. Once stirring was no longer possible owing to the viscosity of the reaction product, the liquid was used for the next reaction step.

2. Condensation Reaction: Synthesis of Diethyl 6-(4-chlorophenoxy)hexylmalonate (6-CPHMA-DEE) in Methanol Substances used:

| | | | |
|---|---|---|---|
| 6-CPHC in 1,6-dichlorohexane | ½ of the batch from the previous synthesis step | | |
| Diethyl malonate | 28 l | 1.5 eq. | 186 mol |
| Potassium carbonate | 35 kg | 2.1 eq. | 253 mol |
| Potassium bromide | 17 kg | 1.2 eq. | 143 mol |
| Methanol | 80 l | | |
| DMF | 75 kg | | |
| 36% strength hydrochloric acid | 5 l | | |
| n-Heptane | 135 kg | | |
| Water | 225 l | | |

Half of the 6-CPHC reaction batch in 1,6-dichlorohexane was distilled under reduced pressure (<10 mbar). The boiling point was preferably kept below 130° C. The distillate was analysed for 1,6-dichlorohexane content and could be used for a further reaction according to step 1.

The residue was analysed for 1,6-dichlorohexane. The distillation was stopped once the content according to gas chromatography was below 20 area %.

After the end of the distillation, the residue was diluted with DMF and transferred to another reactor. Diethyl malonate, potassium carbonate and potassium bromide were added to the DMF solution. The resulting viscous mixture was heated to about 130° C. The reaction mixture was kept at 130° C. for 12–18 hours until the content of starting material according to HPLC was below 1 area %.

The reaction mixture was cooled to 60° C. and the solid was filtered off. The filter cake, which had been sucked dry, was washed with DMF (30 l). n-Heptane (135 kg) and water (150 l) were added to the mother liquor. The mixture was warmed to about 40° C. Using 36% strength hydrochloric acid (about 5 l), the pH was adjusted to pH=2. The aqueous phase was removed and the organic phase was washed with water (75 l).

Following analysis, two reaction batches could be combined. The combined reaction batches were concentrated at a temperature of at most 100° C. When the concentration came to an end, the pressure was reduced to remove as much as possible of the remaining diethyl malonate.

Methanol (80 l) was added to the residue to obtain a concentration suitable for the next reaction.

3. Hydrolysis and Formation of the Double Bond: 8-(4-chlorophenoxy)-2-methyleneoctanoic acid (8-CPMOA)

Substances used:

| | | | |
|---|---|---|---|
| 6-CPHMA-DEE in methanol | Two combined batches from step 2 | | |
| Sodium hydroxide, 50% strength solution | 114 kg | 6 eq. | 1.44 mol |
| Methanol | 280 l | | |
| Water | 1030 l | | |
| n-Heptane | 675 kg | | |
| MTBE (methyl tert-butyl ether) | 280 l | | |
| 36% strength hydrochloric acid | 163 l | | |
| Isopropanol | 440 l | | |
| Paraformaldehyde | 12.5 kg | | |
| Piperidine | 29 l | | |

The sodium hydroxide solution was added to the water/methanol mixture. The temperature of the resulting mixture was adjusted to 50° C. 6-CPHMA-DEE in methanol was added to this mixture. The addition rate was adjusted such that the temperature remained below 52° C. The addition was carried out as quickly as possible. After the addition had ended, water (140 l) was added. Following the addition of water, the reaction was deemed to have been completed. Small amounts of the starting materials could be removed later on in the process.

Methanol was removed under reduced pressure at at most 50° C. During the concentration, water (190 l) was added to ensure that the intermediate remained soluble. n-Heptane (210 kg) and water (100 l) were added, and the mixture was heated to 75° C. The aqueous phase, which contained the product, was removed and transferred into another reactor.

The temperature of the aqueous phase was lowered to below 50° C., and MTBE (280 l) was then added. 36% strength hydrochloric acid (about 130 l) was added to this mixture to adjust the pH to about 1. During the addition of the hydrochloric acid, the temperature was kept below 40° C. The aqueous phase was separated from the organic phase, which was washed with water (190 l) at 40° C.

Isopropanol (290 l) was added to the organic phase. Under reduced pressure, MTBE was removed at at most 40° C. The distillation was continued until the volume which remained in the reactor was about 225 l.

Further isopropanol (150 l) and paraformaldehyde (12.5 kg) were added to the resulting isopropanol solution. The resulting mixture was warmed to about 50° C. To this mixture, piperidine (29 l) was added as quickly as possible, without the temperature exceeding 52° C. This exothermal reaction resulted in a highly viscous reaction mixture.

The reaction was monitored by process-tracking HPLC analysis. Once, after 1–2 hours, less than 10% of free dicarboxylic acid was present, the mixture was heated at reflux. This was continued until, according to HPLC, only negligible amounts (<2%) of the intermediate were present. During the reaction, carbon dioxide was released. A typical reaction time was 3 hours. During the reaction, the viscosity of the reaction mixture was reduced, and towards the end, an almost clear solution was present.

The reaction was deemed to have ended once less than 5 area % (HPLC) of the intermediate was present. By concentration under atmospheric pressure, the volume in the reactor was reduced to about 160 l. Water (270 l) and n-heptane (445 kg) were added to the residue. 36% strength hydrochloric acid (about 33 l) was added until a pH of 1 had been reached. The resulting two-phase system was heated to at least 70° C. The aqueous phase was removed from the organic phase, which was washed with water (140 l) at at least 70° C.

The volume of the organic phase was reduced under reduced pressure and at at most 50° C. The distillation was continued until about 490 l remained in the reactor. Towards the end of the distillation, a temperature of 30° C. was maintained in the reactor. After complete concentration, an 8-CPMOA seed crystal was added.

The reactor content was carefully cooled to 0° C.

The product was isolated by filtration. The filter cake was washed with cold n-heptane (20 kg).

Following filtration, the product could be used directly for the next reaction, without further drying. Each reaction batch gave about 37–40 kg of 8-CPMOA.

4. Amide Formation: 8-CPMOA-Proline

Substances used:

| | | | |
|---|---|---|---|
| 8-CPMOA | 40 kg (dry weight) | | 141 mol |
| Sodium hydroxide, 50% strength solution | 24 l | 3.00 eq. | 423 mol |
| L-proline | 21 kg | 1.30 eq. | 182 mol |
| Water | 85 l | | |
| Ethyl acetate | 85 kg | | |
| Thionyl chloride | 14 l | 1.40 eq. | 198 mol |
| Acetone | 38 kg | | |
| DMF | 106 kg | | |
| MTBE | 154 kg | | |
| 36% strength hydrochloric acid | 25 l | | |
| Sodium chloride | 25 kg | | |
| Water | 76 l | | |

The 8-CPMOA (about 40 kg dry weight) obtained by filtration was added to ethyl acetate (85 kg). From the resulting solution, about 19 l of liquid were evaporated under reduced pressure at at most 40° C. DMF (1 l) was added, and the temperature in the reactor was adjusted to 45° C.

Thionyl chloride (14 l) was added over a period of 60 min. After the end of the addition, the reaction was continued until HPLC showed that all starting material had been consumed. A typical reaction time after the end of the addition was 1–2 hours.

By distillation at at most 45° C., the ethyl acetate and the excess thionyl chloride were removed. Acetone (38 kg) was added, and the resulting mixture was stirred for at least 20 min to obtain complete dissolution.

Sodium hydroxide solution (24 l) and L-proline (21 kg) were added to water (85 l). During the addition of the L-proline, the temperature was kept below 20° C. The solution of the acid chloride and acetone was added to this mixture, the temperature being kept below 20° C. After the end of the addition, the reaction was continued until HPLC showed that all acid chloride had been consumed. A normal reaction time was less than 30 min.

The acetone was evaporated under reduced pressure at at most 40° C. In total, 48 l of liquid were evaporated. MTBE (70 kg) was added, and the resulting two-phase system was warmed to about 40° C. The aqueous phase (which contained product) was removed. Further MTBE (84 kg) was added to the aqueous phase, and the aqueous phase was acidified with 36% strength hydrochloric acid (about 25 l). The pH of the solution was adjusted to a value of 1–2. The temperature of the reactor contents was adjusted to 40° C., and the aqueous phase was removed. The organic phase was washed with a mixture of water (76 l) and sodium chloride (25 kg), at about 40° C.

The MTBE was removed by distillation at at most 40° C. Once the residue had an oily consistency, DMF (105 kg) was added, so that the solution could be used for the next reaction step.

5. Lactone Formation: 8-CPMOA-Lactone

Substances used:

| 8-CPMOA-proline in DMF | 1 batch from the previous reaction step | | |
|---|---|---|---|
| N-Bromosuccinimide (NBS) | 40 kg | 2.05 eq. | 289 mol |
| Potassium tert-butoxide | 16 kg | 1.01 eq. | 143 mol |
| Water | 1350 l | | |
| Sodium thiosulphate | 30 kg | | |
| Sodium carbonate | 17 kg | | |
| DMF | 177 kg | | |
| Ethanol | 400 l | | |
| MTBE | 570 l | | |
| Methanol | 510 l | | |

A solution of NBS (50 kg) and DMF (120 kg) was prepared. To dissolve almost all of the NBS, it was necessary for the DMF to be at room temperature.

Potassium tert-butoxide was added at a temperature of below 50C to the solution of 8-CPMOA-proline in DMF from the previous reaction step. After the end of the addition, the pH of the solution was above 7; if this was not the case, more potassium tert-butoxide was added.

The solution of NBS was added to the solution of 8-CPMOA-proline at such a rate, that the temperature did not exceed 0° C. A typical addition time was 1–2 hours. After the end of the addition, the temperature was increased to 2° C. and maintained at this value for 1 hour. The temperature was increased to 5° C. The mixture was kept at this reaction temperature for about 12–17 hours. During the reaction, a whitish solid was formed.

After the end of the reaction, the reaction solution was cooled to 0° C. The precipitated solid was removed by centrifugation. The centrifugation cake was washed with DMF (57 kg). To obtain all of the products, a fine filtration was carried out. Strict attention was paid to exact temperature control of the mother liquor at a value below 5° C. Owing to its low thermal stability, the solid was immediately suspended in sufficient water.

Water (230 l) and MTBE (570 l) were added to the mother liquor. The addition of water was exothermic, which required the temperature to be kept below 5° C. A solution of sodium thiosulphate (30 kg) in water (120 l) was added. This addition, too, was exothermic. The sodium thiosulphate destroyed the remaining NBS, so that temperature control was no longer required.

The resulting two-phase system was stirred for at least 30 min. The lower phase was then removed. Water (490 l) and sodium carbonate (17 kg) were added, and the reaction mixture was warmed to 40° C. The aqueous phase was removed. The organic phase was washed with water (510 l).

The organic phase was concentrated under atmospheric pressure until about 170 l remained. Methanol (510 l) was added, and the evaporation was continued until the boiling point exceeded 63° C., i.e. until all MTBE had evaporated. By further concentration, the volume in the reactor was adjusted to about 170 l. The product was crystallized by carefully cooling the solution. At about 30° C., the solution was seeded to initiate crystallization. Large amounts of seed crystals were required.

To ensure enantiomeric purity of the end product, a recrystallization was carried out.

Recrystallization of 8-CPMOA-lactone

About 50 kg (dry weight) of 8-CPMOA-lactone (this corresponded to about 1½ batches) were added to ethanol (350 l). By distillation under atmospheric pressure, about 100 l of liquid were evaporated. The solution was cooled to 45° C., so that the solution could be seeded. Here, too, large amounts of seed crystals were required to achieve crystallization. The temperature was lowered slowly to about 15–18° C.

The product was isolated by slow filtration and washed with ethanol. Following filtration, the product was initially dried at room temperature for a number of hours. The temperature was then increased to 40° C. The yield achieved here was 42 kg per recrystallization, which corresponded to about 28 kg per synthesis batch.

6. Release of the Carboxylic Acid: 2-bromoethyl-2-hydroxy-8-(4-chlorophenoxy)octanoic acid (BH-COA)

Substances used:

| 8-CPMOA-lactone | 42 kg | | 92 mol |
|---|---|---|---|
| Toluene | 290 l | | |
| Water | 450 l | | |
| n-Heptane | 20 l | | |
| 36% strength hydrochloric acid | 700 l | 92 eq. | 8400 mol |

8-CPMOA-lactone (42 kg) was added to water (180 l). 36% strength hydrochloric acid (700 l) was added to the suspension.

The mixture was heated at reflux. The reaction was kept at reflux temperature for at least 24 hours and up to 48 hours. Since both starting materials were present as oils, the mixture had to be stirred vigorously.

After the reaction had ended, the reaction mixture was cooled to 75° C. and toluene (270 l) was added. The aqueous phase was removed and the toluene phase was washed with water (270 l) at 75° C.

At a temperature of below 60° C., toluene was removed by distillation until a volume of about 200 l remained. The solution was cooled to about 40–45° C., so that a seed crystal could be added. Once the crystallization had started, the reaction mixture was warmed to about 55° C. and then crystallized by cooling. Cooling was continued up to a temperature of 15° C.

The product was isolated by filtration and then washed with toluene (20 l). The filter cake was washed with n-heptane (20 l).

The crude product could be used without drying for the next reaction step. A typical yield was about 24 kg of BH-COA as calculated dry weight.

7. Synthesis of Etomoxir (Potassium Salt)
   Substances used:

| | | | |
|---|---|---|---|
| BH-COA | 16 kg (dry weight) | | 42 mol |
| Potassium tert-butoxide | 10 kg | 2.11 eq. | 89 mol |
| Water | | | |
| Methanol | 160 l | | |
| MTBE | 315 kg | | |
| Potassium hydroxide | 3 kg | | |
| Water | 160 l | | |

BH-COA (16 kg as dry weight) were added to MTBE (160 kg). The resulting solution was cooled to about 0–5° C. Potassium tert-butoxide was added to this mixture at a rate such that the temperature remained below 5° C. A typical addition time was about 60 min.

After the addition had ended, the reaction was continued (about 30–60 min) until HPLC showed that all of the starting materials had reacted.

After the end of the reaction, water (160 l) was added. The aqueous phase (which contained the product) was removed. MTBE (155 kg) was added to the aqueous phase, and the pH was adjusted with 36% strength hydrochloric acid to a value of 1–2. The temperature of the system was kept at about 40° C.

The aqueous phase was removed and the organic phase was washed with water (160 l) at about 40° C.

MTBE was removed by distillation under reduced pressure at about 40° C. until a volume of about 100 l remained. Methanol (120 l) was added and the distillation was continued until the residual volume was about 60 l.

A solution of potassium hydroxide (3 kg) and methanol (30 l) was added to the methanolic solution. During the addition, the product precipitated as potassium salt. After the end of the addition, the viscous mixture was cooled to about 0° C.

The product was isolated by centrifugation and then washed with methanol (10 l). The product obtained by centrifugation was dried at 35° C. A typical dry yield was about 12 kg.

8. Esterification: Synthesis of (+)-Etomoxir
   Substances used:

| | | | |
|---|---|---|---|
| Etomoxir, potassium salt | 3.5 kg | | 10.4 mol |
| Ethyl bromide | 1.7 kg | 1.50 eq. | 15.6 mol |

-continued

| | |
|---|---|
| n-Heptane | 39 l |
| Water | 44 l |
| Sodium carbonate | 1.2 kg |
| DMF | 16 l |
| Ethanol | 400 l |

Ethyl bromide (1.7 kg) was added to DMF (14 l). The mixture was warmed to 38° C. Etomoxir potassium salt was added to the mixture at a rate such that no lumps were formed.

The reaction was continued at 40° C. for about 18–20 hours until HPLC showed that the starting materials had been consumed. During the reaction time, the reaction mixture became less and less viscous, and at the end of the reaction, only a small precipitate of potassium bromide was present.

The precipitate was removed by filtration and the filter cake was washed with DMF (2 l). n-Heptane (14 l) and water (14 l) were added to the mother solution. The two-phase system was heated to 50° C. and the aqueous phase was removed. n-Heptane (10 l) was added to the organic phase. The organic phase was washed at 50° C. first with water (15 l) and sodium carbonate (1.2 kg) and then with water (15 l).

10 l of n-heptane were distilled off under reduced pressure at at most 50° C. The product mixture was filtered off with suction through a fine filter. The fine filter was then rinsed with n-heptane (10 l).

From the filtered solution, 14 l of n-heptane were distilled off under reduced pressure at at most 50° C. The solution was cooled to about 19–20° C. so that seeding could be carried out. To prevent the formation of an oil, the mixture was stirred at high speed during the crystallization. After seeding of the solution, the solution was cooled very carefully to about −5° C.

The product was isolated by filtration and washed with 5 l of n-heptane at a temperature of below 0° C. The product was carefully sucked dry, since (+)-etomoxir melts at about 35° C. and had to be treated very carefully.

The product was dried under reduced pressure at at most 20° C. A typical yield was 2.4 kg of (+)-etomoxir.

Example 2

The general synthesis of the oxiranecarboxylic acids corresponded to that of Example 1 described above. However, in the first reaction step, the amount of 1,6-dichlorohexane was reduced from 7.9 to 3 equivalents to increase the yield of the reaction process and to reduce the raw material costs. This modification did result in an increased formation of the byproduct 1,6-bis-(4-chlorophenyl)hexane; however, this was easily removed in step 3. For further processing, water was added to the reaction mixture and the product was extracted with MTBE. In this way, the filtration originally required became redundant.

Example 3

In this example, too, the general synthesis of the oxiranecarboxylic acids corresponded to the reaction scheme described in Example 1, if appropriate with the modification according to Example 2. However, instead of potassium carbonate, sodium ethoxide was used as starting material for the reaction. The result of this modification was that the reaction had finished after only 3–4 hours and not as before after 18 hours. Moreover, the reaction required a lower temperature and had the advantage that fewer byproducts were formed.

Example 4

In this example, too, the general synthesis of the oxiranecarboxylic acids corresponded to the reaction scheme described in Example 1, if appropriate with the modification according to Example 2. Instead of potassium carbonate, sodium ethoxide was, according to Example 3, used as starting material for the reaction. In the lactone formation according to step 5, the end product was purified by recrystallization from a mixture of isopropanol and heptane; further recrystallization was not required.

For the final release of the carboxylic acid according to step 6, 50% strength sulphuric acid was used instead of hydrochloric acid.

Example 5

In this example, too, the general synthesis of the oxiranecarboxylic acids corresponded to the reaction scheme described in Example 1, if appropriate with the modifications according to Examples 2, 3 and/or 4. However, 8-CP-MOA-lactone was heated by heating at 125–130° C. in a mixture of water and sulphuric acid for 8–12 hours. The product was isolated analogously to the process described; however, the toluene solution was, after drying and concentration by azeotropic distillation, used for the next step without further processing. By this, it was possible to prevent the formation of chlorinated byproducts, which resulted in an increased yield, a shorter reaction time and a simplified process.

The solution thus obtained was then treated with potassium tert-butoxide. The reaction product was worked up analogously to the process described; however, instead of hydrochloric acid, dilute phosphoric acid was used. For precipitating the product, the solvent used was n-propanol and instead of potassium hydroxide and methanol, an aqueous solution of potassium carbonate was used. The solution of the potassium salt of the reaction product in n-propanol was then heated until an almost clear solution was obtained. The product was collected by filtration at or below room temperature and then dried. Subsequently, the product was recrystallized from ethanol. These modifications of the last process step resulted in improved filtration properties of the material, which in the end also led to an increased quality of the product.

What is claimed is:

1. A process for preparing oxiranecarboxylic acids and derivatives thereof, comprising the synthesis of a compound of the formula (X):

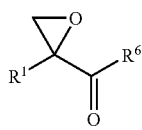

(X)

in which

R$^1$ is a straight-chain or branched mono-, poly-, or unsubstituted alkyl group; a straight-chain or branched mono-, poly-, or unsubstituted alkylene group;, a straight-chain or branched mono-, poly-, or unsubstituted aralkyl or alkylaryl group; or a mono-, poly- or unsubstituted aryl group, and R$^6$ is selected from the group consisting of OH; O$^-$M$^+$; O$^-$M$^{2+}$, where M is an alkali metal, an alkaline earth metal, an earth metal, or a cation of an organic nitrogen base; and OR, where R is a substituted or unsubstituted alkyl or alkylene group having 1 to 15 carbon atoms, comprising the steps:

(a) reacting a compound of the formula (V) with an amine of the formula (VI) to give a compound of the formula (VII):

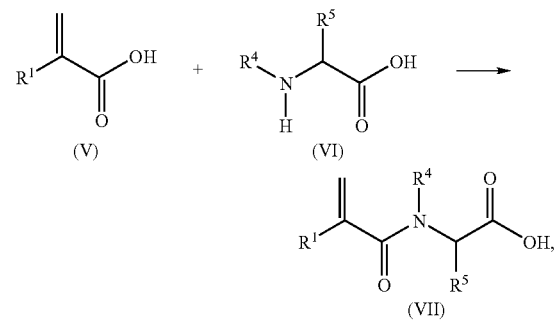

in which

R$^1$ is as defined above, and

R$^4$ and R$^5$ are identical or different straight-chain or branched mono-, poly-, or unsubstituted alkyl groups; straight-chain or branched mono-, poly-, or unsubstituted alkylene groups; straight-chain or branched mono-, poly-, or unsubstituted aralkyl or alkylaryl groups; or mono-, poly-, or unsubstituted aryl groups, where R$^4$NCR$^5$ may be part of a substituted or unsubstituted cyclic structure which may contain a heteroatom selected from the group consisting of N, S, and O;

(b) converting a compound of the formula (VII) into a lactone of the formula (VIII):

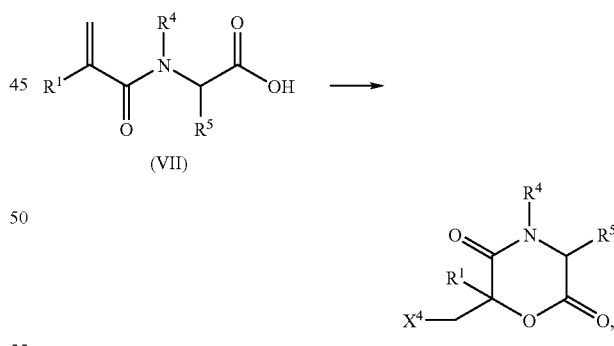

in which

R$^1$, R$^4$, and R$^5$ are as defined above,

R$^1$ and R$^4$NCR$^5$ are not simultaneously —(CH$_2$)$_6$—OBn, wherein Bn represents benzyl, and an unsubstituted five-membered ring, respectively, and X$^4$ is a functional group capable of forming a cationic intermediate in a reaction with a C—C double bond and is a good leaving group;

(c) converting a lactone of the formula (VIII) into a compound of the formula (IX):

(VIII) → (IX)

in which
R$^1$, R$^4$, R$^5$, R$^6$, and X$^4$ are as defined above, and
R$^1$ and R$^4$NCR$^5$ are not simultaneously —(CH$_2$)$_6$—OBn, wherein Bn represents benzyl, and an unsubstituted five-membered ring, respectively; and (d) converting a compound of the formula (IX) into the compound of the formula (X):

(IX) → (X)

in which R$^1$, R$^6$, and X$^4$ are as defined above.

2. The process according to claim 1, characterized in that the compound of the formula (V) is obtained by reacting a compound of the formula (IV):

(IV)

where in the formula (IV), R$^1$ is a straight-chain or branched mono-, poly-, or unsubstituted alkyl group; a straight-chain or branched mono-, poly-, or unsubstituted alkylene group; a straight-chain or branched mono-, poly-, or unsubstituted aralkyl or alkylaryl group; or a mono-, poly-, or unsubstituted aryl group.

3. The process according to claim 2, characterized in that the compound of the formula (IV) is obtained by hydrolysing the compound of the formula (III):

(III)

in which
R$^1$ is a straight-chain or branched mono-, poly-, or unsubstituted alkyl group; a straight-chain or branched mono-, poly-, or unsubstituted alkylene group; a straight-chain or branched mono-, poly-, or unsubstituted aralkyl or alkylaryl group; or a mono-, poly-, or unsubstituted aryl group, and
Y$^1$ and Y$^2$ are identical or different electron-withdrawing groups which can be converted into a carboxylic acid.

4. The process according to claim 3, characterized in that the compound of the formula (III) is obtained by condensing a compound of the formula (I) with a compound of the formula (II):

(I) + (II) → (III)

in which
R$^1$ is a straight-chain or branched mono-, poly-, or unsubstituted alkyl group; a straight-chain or branched mono-, poly-, or unsubstituted alkylene group; a straight-chain or branched mono-, poly-, or unsubstituted aralkyl or alkylaryl group; or a mono-, poly-, or unsubstituted aryl group,
X$^1$ is a leaving group,
Y$^1$ and Y$^2$ are identical or different electron-withdrawing groups which can be converted into a carboxylic acid.

5. The process according to claim 4, characterized in that the compound R$^1$—X$^1$ of the formula (I) is obtained by reacting a straight-chain or branched mono- or polysubstituted alkane having two leaving groups, X$^1$ and X$^2$, with a mono-, poly-, or unsubstituted benzene derivative.

6. The process according to claim 4, characterized in that the substituents are, independently of one another, defined as follows:
R$^1$ is a group containing 1 to 20 carbon atoms, unsubstituted or substituted with one or more halogens such as fluorine,
R$^4$ and R$^5$ are part of a substituted or unsubstituted cyclic structure R$^4$NCR$^5$ which may contain a heteroatom selected from the group consisting of N, S, and O, which may be included in a five- or six-membered ring,
X$^1$ is a halogen atom, such as chlorine or bromine, a tosylate group, or a triflate group,
X$^4$ is a halogen atom selected from the group consisting of chlorine, bromine, and iodine,
R$^6$ is selected from the group consisting of OH, O$^-$Na$^+$, O$^-$K$^+$, O$^-$Li$^+$, and OR,
where R is an unsubstituted alkyl group containing 1 to 10 carbon atoms, and
Y$^1$ and Y$^2$ are selected from the group consisting of CN, carboxylic acid, carboxylic anhydride, and carboxylic ester with a C$_1$- to C$_{10}$-alcohol.

7. The process according to claim 1, characterized in that R$^1$ has a structure of the formula (1a):

(1a)
—(CR'R")$_n$—Z$_m$— in which
R' and R" are hydrogen, fluorine, or methyl groups,
L' and L" are, independently, hydrogen, halogen, a substituted or unsubstituted branched or straight-chain alkyl or alkylaryl group, a substituted or unsubstituted branched or straight-chain alkoxy group, a substituted or unsubstituted aryloxy group, a substituted or unsubstituted branched or straight-chain carboxyalkyl group, a substituted or unsubstituted carboxyaryl group, a nitro group, or a trifluoromethyl group, Z is —P(CR'R")$_o$—, where P is oxygen or sulphur and o is an integer from 0 to 4, m is an integer from 0 to 2, and n is an integer from 2 to 8.

8. The process according to claim 7, characterized in that L' or L" is hydrogen and the other substituent L' or L" is a halogen atom, m and o are 1, n is 6, and P is oxygen.

9. The process according to claim 1, characterized in that the compound of the formula (VI) is proline or a derivative thereof.

10. The process according to claim 1, characterized in that the compound of the formula (VI) is L-proline, $X^4$ is a functional group capable of forming a cationic intermediate in a reaction with a C—C double bond and is a good leaving group, and $R^6$ is selected from the group consisting of OH; $O^-M^+$; $O^-M^{2+}$, where M is an alkali metal, an alkaline earth metal, an earth metal, or a cation of an organic nitrogen base; and OR, where R is a substituted or unsubstituted alkyl or alkylene group having 1 to 15 carbon atoms.

11. The process according to claim 1, characterized in that the individual reaction steps are carried out under stereochemical control.

12. The process according to claim 1, for preparing etomoxir, palmoxirate, or clomoxir.

13. The process according to claim 1, for preparing (+)-etomoxir.

* * * * *

UNITED STATES PATENT AND TRADEMARK OFFICE
CERTIFICATE OF CORRECTION

| | |
|---|---|
| PATENT NO. | : 7,078,543 B2 |
| APPLICATION NO. | : 10/473503 |
| DATED | : July 18, 2006 |
| INVENTOR(S) | : Cernerud et al. |

It is certified that error appears in the above-identified patent and that said Letters Patent is hereby corrected as shown below:

Column 15, Line 56, replace "below 50C" with --below 5°C--.

Signed and Sealed this

Twenty-ninth Day of July, 2008

JON W. DUDAS
*Director of the United States Patent and Trademark Office*